US011266757B2

(12) United States Patent
Schumaier

(10) Patent No.: US 11,266,757 B2
(45) Date of Patent: Mar. 8, 2022

(54) HEARING AID DRYER AND DISINFECTION KIT WITH UV-REFLECTIVE DRYING TRAY

(71) Applicant: Daniel R. Schumaier, Elizabethton, TN (US)

(72) Inventor: Daniel R. Schumaier, Elizabethton, TN (US)

(*) Notice: Subject to any disclaimer, the term of this patent is extended or adjusted under 35 U.S.C. 154(b) by 0 days.

(21) Appl. No.: 17/398,200

(22) Filed: Aug. 10, 2021

(65) Prior Publication Data
US 2021/0361803 A1 Nov. 25, 2021

Related U.S. Application Data

(63) Continuation-in-part of application No. 16/671,480, filed on Nov. 1, 2019, now Pat. No. 11,102,588,
(Continued)

(51) Int. Cl.
*A61L 2/10* (2006.01)
*A61L 2/26* (2006.01)
(Continued)

(52) U.S. Cl.
CPC *A61L 2/10* (2013.01); *A61L 2/26* (2013.01); *F26B 5/16* (2013.01); *F26B 9/003* (2013.01);
(Continued)

(58) Field of Classification Search
CPC combination set(s) only.
See application file for complete search history.

(56) References Cited

U.S. PATENT DOCUMENTS

| 5,404,105 A | 4/1995 | Chari |
| 5,416,886 A | 5/1995 | Zahler |

(Continued)

FOREIGN PATENT DOCUMENTS

| CN | 201018665 | 2/2008 |
| CN | 103747388 A | 4/2014 |

(Continued)

OTHER PUBLICATIONS

Ear Technology Corporation, Dry & Store Global Operation, Oct. 2005, pp. 1-7. (Year: 2005).

*Primary Examiner* — Angelica M McKinney
(74) *Attorney, Agent, or Firm* — Luedeka Neely Group, P.C.

(57) ABSTRACT

A portable dryer and disinfection device includes a container having an interior for receiving one or more electronic components for drying and disinfection. A lid is configured to be removably secured to an upper portion of the container. An ultraviolet light source is attached to a bottom portion of the lid, wherein ultraviolet light generated by the ultraviolet light source is directed into the interior of the container below the lid. A power source is disposed in the lid for providing electrical power to the ultraviolet light source. A tray is disposed within the interior of the container on which the one or more electronic components are placed for drying and disinfection. The tray includes holes that provide air flow communication through the removable tray. A removable desiccant holder is disposed at least partially within the interior of the container below the tray.

20 Claims, 7 Drawing Sheets

Related U.S. Application Data which is a continuation-in-part of application No. 16/532,868, filed on Aug. 6, 2019, now Pat. No. 11,122,378.

(51) Int. Cl.
*H04R 25/00* (2006.01)
*F26B 9/00* (2006.01)
*F26B 5/16* (2006.01)

(52) U.S. Cl.
CPC .......... *H04R 25/65* (2013.01); *A61L 2202/11* (2013.01); *A61L 2202/122* (2013.01); *A61L 2202/14* (2013.01); *A61L 2202/16* (2013.01); *H04R 2460/17* (2013.01)

(56) References Cited

U.S. PATENT DOCUMENTS

| | | | |
|---|---|---|---|
| 5,640,783 A | 6/1997 | Schumaier | |
| 5,852,879 A * | 12/1998 | Schumaier | A61L 2/07 34/80 |
| D414,304 S | 9/1999 | Schumaier | |
| 6,399,920 B1 | 6/2002 | Guinn | |
| D467,394 S | 12/2002 | Schumaier | |
| 6,625,900 B1 | 9/2003 | Tobias | |
| 7,062,057 B2 | 6/2006 | Wu | |
| D536,491 S | 2/2007 | Schumaier | |
| 7,182,820 B2 | 2/2007 | Campbell et al. | |
| 7,195,177 B2 | 3/2007 | Haws et al. | |
| 8,112,900 B2 | 2/2012 | Romanek | |
| 8,689,461 B1 | 4/2014 | Cookson et al. | |
| D786,515 S | 5/2017 | Pindzola et al. | |
| D786,516 S | 5/2017 | Pindzola et al. | |
| 9,709,327 B2 | 7/2017 | Marchiori | |
| 9,839,707 B2 | 12/2017 | Won | |
| 9,843,870 B2 | 12/2017 | Naumann | |
| 11,092,379 B2 | 8/2021 | Schumaier et al. | |
| 2003/0196687 A1 | 10/2003 | Campbell et al. | |
| 2004/0073275 A1 | 4/2004 | Maltan et al. | |
| 2004/0118427 A1 | 6/2004 | Palfy et al. | |
| 2004/0258559 A1 | 12/2004 | Paskal et al. | |
| 2005/0189354 A1 | 9/2005 | Heather et al. | |
| 2006/0220620 A1 | 10/2006 | Aradachi et al. | |
| 2008/0175761 A1 | 7/2008 | Thur et al. | |
| 2009/0080679 A1 | 3/2009 | Rass | |
| 2009/0296968 A1 * | 12/2009 | Wu | H04R 25/00 381/323 |
| 2010/0011613 A1 | 1/2010 | Husung | |
| 2010/0088916 A1 | 4/2010 | Romanek | |
| 2010/0088922 A1 | 4/2010 | Romanek | |
| 2011/0049391 A1 * | 3/2011 | Yang | A61L 2/10 250/492.1 |
| 2012/0006995 A1 * | 1/2012 | Greuel | A61L 2/10 250/373 |
| 2012/0216418 A1 | 8/2012 | Serman et al. | |
| 2013/0004367 A1 | 1/2013 | Roberts | |
| 2013/0330235 A1 | 12/2013 | Stibich et al. | |
| 2014/0175280 A1 | 6/2014 | Tantillo | |
| 2014/0270896 A1 * | 9/2014 | Green | A45D 40/02 401/143 |
| 2015/0162770 A1 | 6/2015 | Choi et al. | |
| 2015/0174426 A1 | 6/2015 | Germain et al. | |
| 2015/0250646 A1 * | 9/2015 | Lipford | A61F 7/12 424/613 |
| 2016/0008498 A1 | 1/2016 | Boysset et al. | |
| 2016/0074545 A1 | 3/2016 | Kim | |
| 2016/0101202 A1 | 4/2016 | Gil et al. | |
| 2016/0165367 A1 | 6/2016 | Ochsenbein | |
| 2016/0277848 A1 | 9/2016 | Naumann | |
| 2016/0301287 A1 | 10/2016 | Nagata et al. | |
| 2016/0302567 A1 | 10/2016 | Gorelick | |
| 2017/0023299 A1 | 1/2017 | Leung et al. | |
| 2017/0347473 A1 | 11/2017 | Freer et al. | |
| 2018/0066890 A1 | 3/2018 | Zielinski et al. | |
| 2018/0123355 A1 | 5/2018 | Olson et al. | |
| 2018/0123367 A1 | 5/2018 | Higgins et al. | |
| 2019/0142981 A1 * | 5/2019 | Kim | G01B 11/02 250/455.11 |
| 2019/0167827 A1 | 6/2019 | Gaska et al. | |
| 2019/0208342 A1 | 7/2019 | Higgins et al. | |
| 2019/0241046 A1 | 8/2019 | Chiu | |
| 2019/0297437 A1 * | 9/2019 | Gil | F26B 9/003 |
| 2020/0015518 A1 * | 1/2020 | Lopez | A24F 19/10 |
| 2020/0205245 A1 | 6/2020 | Ma et al. | |
| 2020/0267483 A1 | 8/2020 | Schumaier | |
| 2021/0022473 A1 * | 1/2021 | Hurter | A45D 29/00 |

FOREIGN PATENT DOCUMENTS

| | | | |
|---|---|---|---|
| CN | 203589776 U | | 5/2014 |
| CN | 104534822 A | | 4/2015 |
| CN | 204395050 U | | 6/2015 |
| CN | 205457846 U | | 8/2016 |
| CN | 205901402 U | | 1/2017 |
| CN | 208770000 | * | 4/2019 |
| CN | 208770000 U | | 4/2019 |
| DE | 202017107151 U1 | | 1/2018 |
| KR | 20060012144 A | | 2/2006 |
| KR | 20120085980 A | | 8/2012 |
| KR | 101466886 B1 | | 12/2014 |
| WO | 1998048855 A1 | | 11/1998 |
| WO | 2007066908 A1 | | 6/2007 |
| WO | 2015104894 A1 | | 7/2015 |

\* cited by examiner

HEARING AID DRYER AND DISINFECTION KIT WITH UV-REFLECTIVE DRYING TRAY

RELATED APPLICATIONS

This application claims priority as a continuation-in-part to co-pending U.S. patent application Ser. No. 16/671,480 titled HEARING AID DRYER AND DISINFECTION KIT, filed Nov. 1, 2019. This application also claims priority as a continuation-in-part to co-pending U.S. patent application Ser. No. 16/532,868 titled HEARING AID DRYER AND DISINFECTION KIT, filed Aug. 6, 2019. The entire contents of the prior filed applications are incorporated herein by reference.

TECHNICAL FIELD

The disclosure relates to a portable drying device for drying electronic and nonelectronic components, and in particular to a hearing aid drying and disinfection kit.

BACKGROUND AND SUMMARY

A hearing aid patient relies on a hearing aid device, and thus its components, to reliably function. Hearing aid devices comprise numerous sensitive electronic components that require periodic maintenance. These components may include a receiver, microphone, volume control, potentiometers, contacts, rechargeable batteries, and circuitry.

Hearing aid devices are subject to a moist environment when worn by a user. Moisture alone may negatively impact device performance and longevity particularly with regard to the electronic components. Moisture also aggravates the buildup of ear wax, dirt, and grime, which may also deteriorate performance and longevity.

Untreated moisture may, for example, cause corrosion on contacts, potentiometers, circuitry, batteries, and wires, condensation on screens or diaphragms in the microphone/receiver, and/or loss of sensitivity of or change in the frequency response of the microphone/receiver. Further, untreated moisture and buildup may lead to ear infections.

Reducing moisture content and/or facilitating the removal of buildup and bacteria, assists in the reliable functionality, maintainability, cleanliness, and longevity of hearing aid devices and prevents unwanted ear infections. Many hearing aid maintenance systems are rather large and expensive and may not be conveniently carried in a purse, suitcase, or brief-case. Accordingly, there is a need for a simple, relatively small, portable, battery-powered, and inexpensive hearing aid maintenance kit that reduces moisture and disinfects the hearing aids.

In view of the foregoing, an embodiment of the disclosure provides an electronic component dryer device including a container having an interior portion for receiving one or more electronic components for drying, a desiccant disposed in the interior portion of the container, and a removable lid for the container. The removable lid contains a disinfecting light source, and a power source for providing power to the disinfecting light source. Light generated by the disinfecting light source is directed into the interior portion of the container.

In another embodiment there is provided an improved electronic component dryer kit that includes an air-tight container and a removable desiccant. The improvement includes a removable lid for the container, wherein the removable lid contains a disinfecting light source, and a power source for providing power to the disinfecting light source. The light generated by the disinfecting light source is directed into the interior portion of the container.

In some embodiments, the removable lid includes a controller circuit that is isolated from the interior portion of the container, wherein the controller circuit controls the disinfecting light source to operate for a predetermined period of time. In other embodiments, the predetermined period of time can be controlled by firmware in the processor to range from minutes to hours.

In some embodiments, wherein the removable lid also includes a switch that is isolated from the interior portion of the container for activating the disinfecting light source. In other embodiments, the switch comprises a capacitive switch. In still other embodiments, the capacitive switch is on a top portion of the removable lid.

In some embodiments, the disinfecting light source comprises an ultraviolet light source. In other embodiments, the ultraviolet light source includes one more ultraviolet light emitting diodes or one or more ultraviolet lamps.

In some embodiments, the removable lid also includes a power on/off indicator.

In some embodiments, the removable lid is an air-tight removable lid.

In some embodiments, the desiccant is a replaceable desiccant holder containing desiccant and having vent holes therein.

In some embodiments, the dryer device includes lid removal detection circuitry comprising a magnetic switch or metal contacts on the container and the lid that closes a circuit to provide power to the disinfecting light source when lid is secured to the container.

In some embodiments, the controller circuit generates an indication that the desiccant is due for replacement.

In some embodiments, the dryer device includes an indicator lamp disposed on the removable lid, and the indication that the desiccant is due for replacement comprises changing a property of light generated by the indicator lamp.

In another aspect, embodiments of the invention provide a portable dryer and disinfection device comprising a container having an interior for receiving one or more electronic components for drying and disinfection, and a lid configured to be removably secured to an upper portion of the container. An ultraviolet light source is attached to a bottom portion of the lid, wherein ultraviolet light generated by the ultraviolet light source is directed into the interior of the container below the lid. A power source is disposed in the lid for providing electrical power to the ultraviolet light source. A tray is disposed within the interior of the container on which the one or more electronic components are placed for drying and disinfection. The tray includes holes that provide air flow communication through the tray. A removable desiccant holder is disposed at least partially within the interior of the container below the tray.

In some embodiments, the portable dryer and disinfection device includes a top portion configured to be removably secured to an upper portion of the lid.

In some embodiments, the portable dryer and disinfection device includes a cycle start switch disposed in the lid and isolated from the interior of the container. The cycle start switch includes a pushbutton portion extending above the upper portion of the lid, and the top portion of the device includes a central aperture through which the pushbutton portion of the cycle start switch extends when the top portion is secured to the upper portion of the lid.

In some embodiments, the power source comprises one or more replaceable batteries disposed in a recess in an upper portion of the lid, and the top portion of the device is configured to be removed from the upper portion of the lid to provide access for removal and replacement of the one or more replaceable batteries.

In some embodiments, the portable dryer and disinfection device includes a bottom portion configured to be removably secured to a bottom lip of the container. The bottom portion is configured to be removed from the container to provide access for removal and replacement of the removable desiccant holder.

In some embodiments, the portable dryer and disinfection device includes a controller circuit disposed within the lid and isolated from the interior of the container. The controller circuit is configured to control the ultraviolet light source to operate during a drying and disinfection cycle.

In some embodiments, the controller circuit generates an indication that the desiccant holder is due for replacement.

In some embodiments, the portable dryer and disinfection device includes an indicator lamp disposed on the lid, and the indication generated by the controller circuit comprises changing a property of light generated by the indicator lamp.

In some embodiments, the ultraviolet light source comprises one more ultraviolet light emitting diodes or one or more ultraviolet lamps.

In some embodiments, an interface between the lid and the container provides an air-tight seal.

In some embodiments, the portable dryer and disinfection device includes lid removal detection circuitry that deactivates the ultraviolet light source upon removal of the lid from the container. The lid removal detection circuitry may comprise a magnetic switch or metal contacts on the container and on the lid that closes a circuit to provide power to the ultraviolet light source when lid is secured to the container.

In some embodiments, the tray is configured to be removable from the interior of the container.

In some embodiments, the tray has an ultraviolet-reflective coating on at least an upper surface thereof.

BRIEF DESCRIPTION OF THE DRAWINGS

The invention will be further understood from the drawings herein of certain preferred embodiments, wherein the structures are not drawn to scale, and the following description thereof, wherein.

DESCRIPTION OF THE PREFERRED EMBODIMENTS

First Embodiment

Figure 1A:
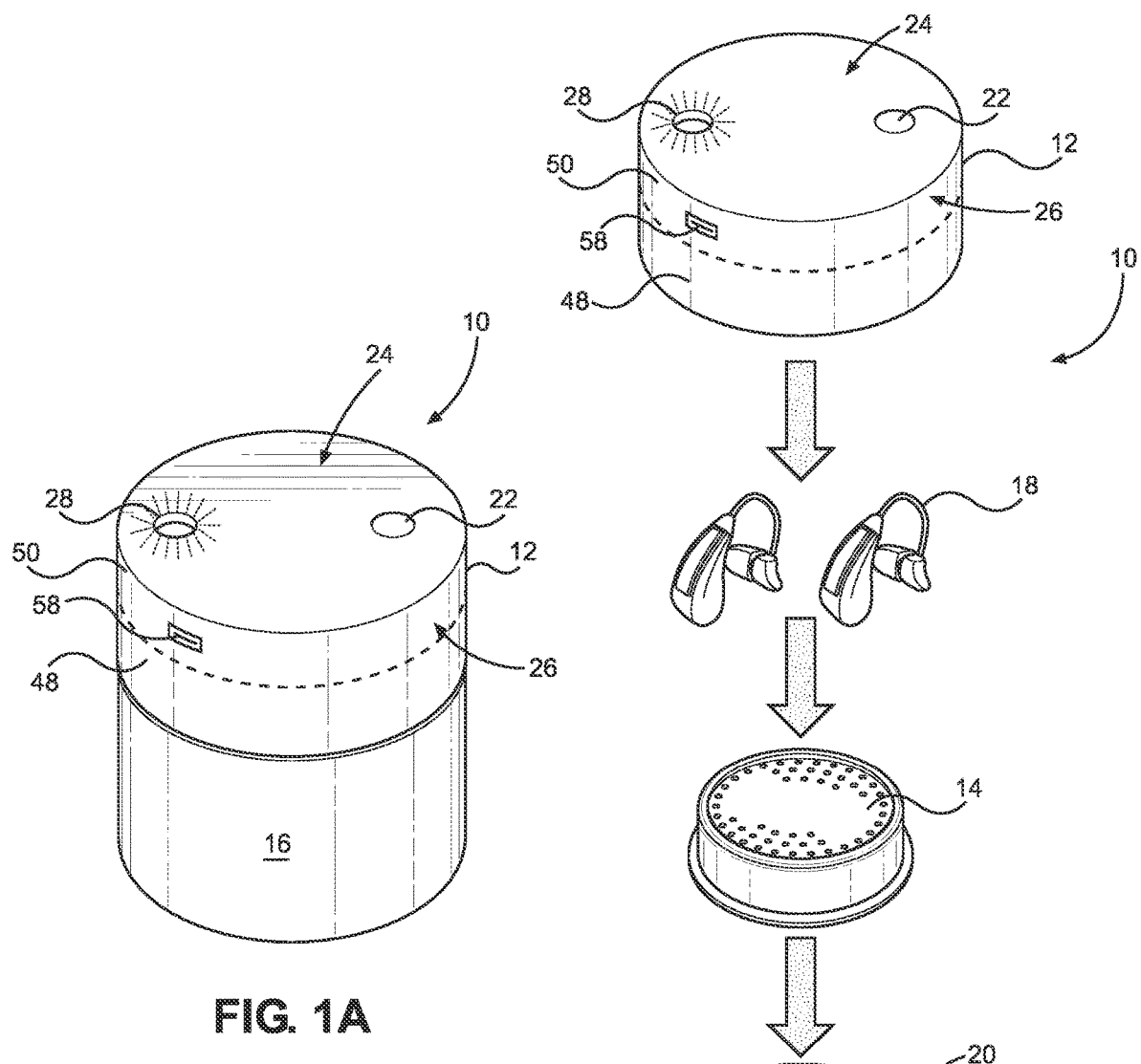
FIG. 1A is a perspective view of a hearing aid dryer and disinfection kit according to a first embodiment.
Figure 1B:
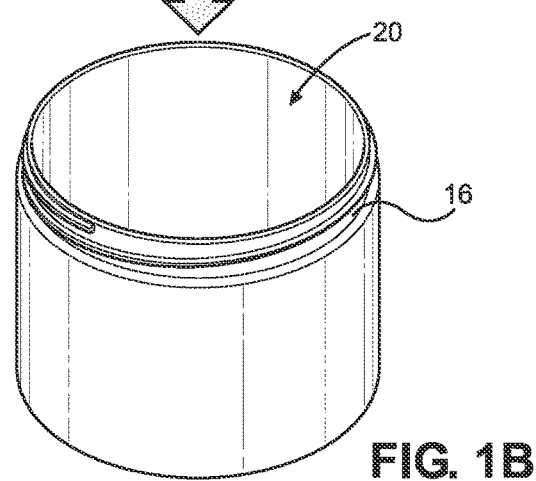
FIG. 1B is an exploded perspective view of the hearing aid dryer and disinfection kit of FIG. 1A.

With reference to FIGS. 1A and 1B there are illustrated a perspective view and an exploded view of an electronic component dryer and disinfection device 10 showing the primary components thereof. In various embodiments, the device 10 may be used to dry and disinfect various types of electronic components, including but not limited to hearing aids, personal sound amplifiers, ear buds, and in-ear monitors. The device 10 includes a removable lid 12, a removable desiccant holder 14 containing desiccant, and a container 16 for holding hearing aids 18 to be dried and disinfected. An interior 20 of the container 16 is sized to contain the desiccant holder 14 and the hearing aids 18 during a drying and disinfection procedure. The disinfection procedure is initiated by a cycle start switch 22 on a top portion 24 or side portion 26 of the lid 12. During the disinfection procedure, an indicator lamp 28 attached to the lid 12, such as an LED lamp, may be illuminated to warn a user not to remove the lid 12 of the device 10 until the disinfection step is completed.

The lid 12, desiccant holder 14 and container 16 may have a cylindrical shape to facilitate a screw-on or snap-on lid 12. However, any other shaped container, lid and desiccant holder may be used including square or rectangular shaped lids, desiccant holders and containers. The lid 12 may also provide an air-tight seal when attached to the container 16 so that ambient moisture external to the device 10 is avoided. An O-ring type gasket may be included for the purpose of providing the air-tight seal.

Figure 2A:
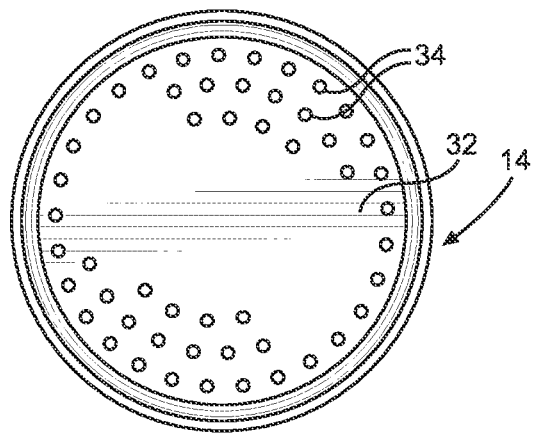
FIG. 2A is a top plan view of a removable desiccant for the hearing aid dryer and disinfection kit according to a preferred embodiment.
Figure 2B:
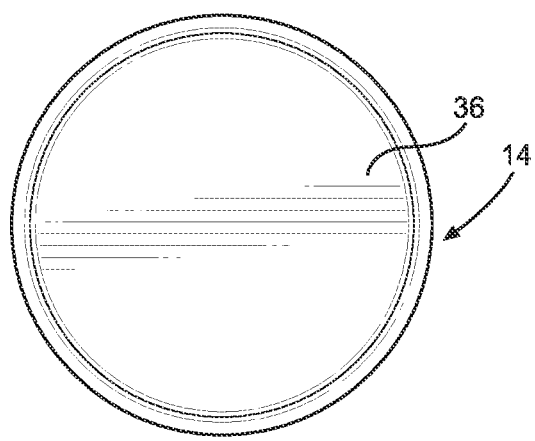
FIG. 2B is a bottom plan view of the removable desiccant for the hearing aid dryer and disinfection kit according to a preferred embodiment.

FIG. 2A is a top, plan view, of the desiccant holder 14 containing desiccant. The desiccant may include any moisture absorbing material such as supported granular CaO, $CaCl_2$, $ZnCl_2$, $CUSO_4$, silica gel or the like. The amount of desiccant in the desiccant holder 14 may be sufficient to dry hearing aids for a month or more. A top side 32 of the desiccant holder 14 has a plurality of vent holes 34 therein for transferring moisture from the hearing aids 18 to desiccant in the desiccant holder 14. A bottom side 36 of the desiccant holder 14, as shown in FIG. 2B is devoid of vent holes.

Figure 3:
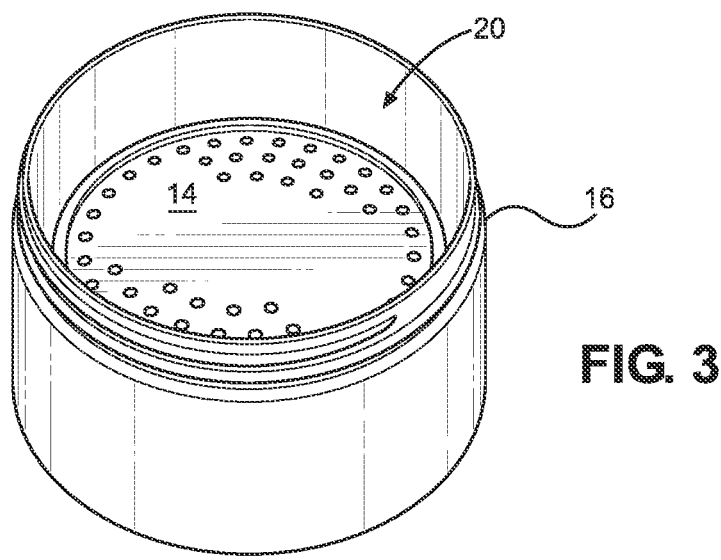
FIG. 3 is a perspective view of a container for the hearing aid dryer and disinfection kit of FIGS. 1A and 1B with a removable desiccant disposed in the container.
Figure 4:
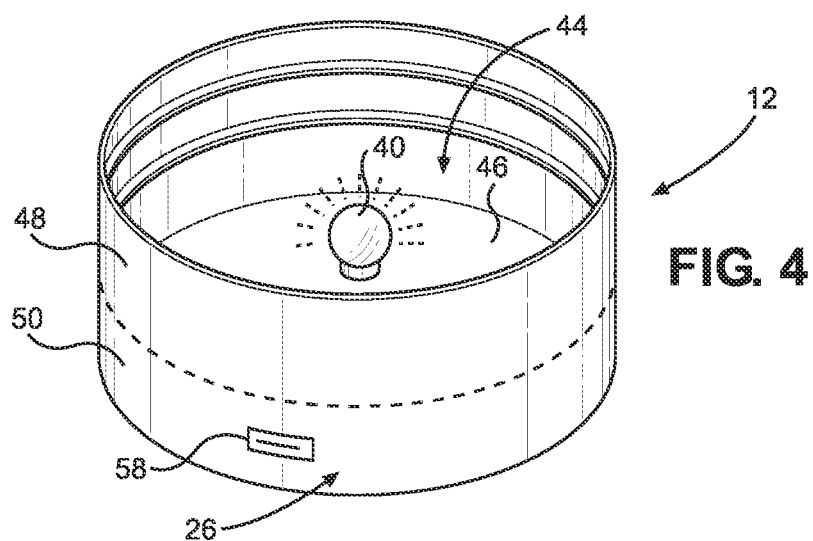
FIG. 4 is a perspective view of an inside portion of the lid for the container of the hearing aid dryer and disinfection kit of FIGS. 1A and 1B.
Figure 5:
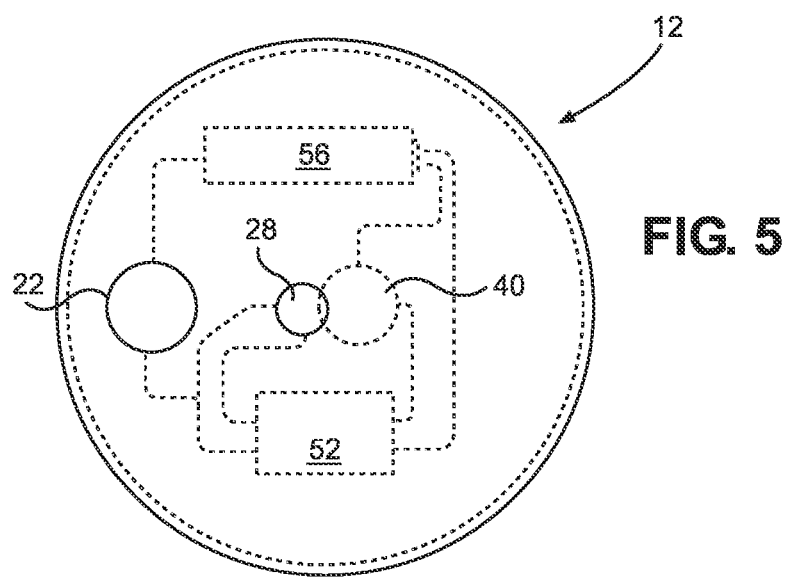
FIG. 5 is a plan view of electrical components within the lid of FIG. 4.
Figure 6:
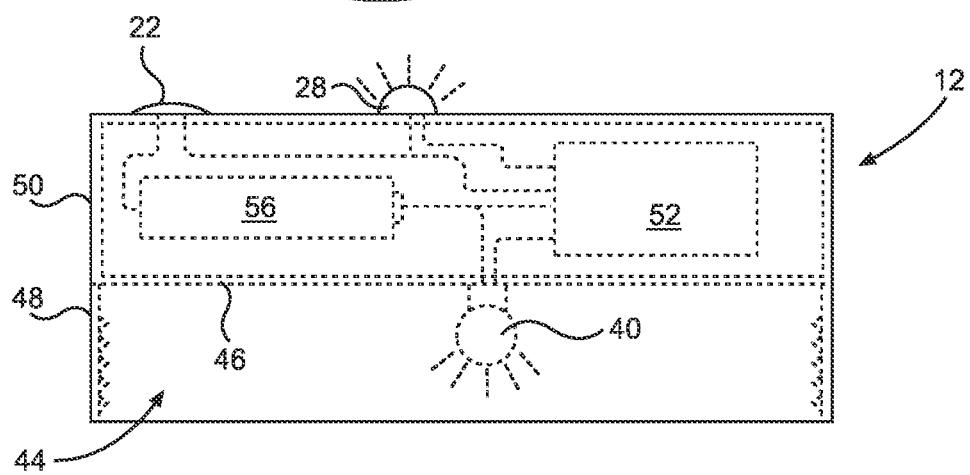
FIG. 6 is a cross-sectional elevation view of the lid of FIGS. 4 and 5.

FIG. 3 illustrates the desiccant holder 14 disposed in the interior 20 of the container 16. The container 16 has an overall interior size that is suitable for accommodating the desiccant holder 14 and one or more hearing aids 18 therein to be dried and disinfected. In some embodiments, the desiccant may be spherical in shape and disposed in a bottom portion of the container 16 with or without a separate desiccant holder 14. In some embodiments, the container 16 may be a two part container having desiccant disposed in bottom portion of the container and the hearing aids 18 disposed in a top portion of the container wherein the hearing aids 18 are separated from the desiccant by a foraminous separator. In other embodiments, the hearing aids 18 may be disposed in direct contact with the desiccant in the absence of a desiccant holder.

Figure 7:
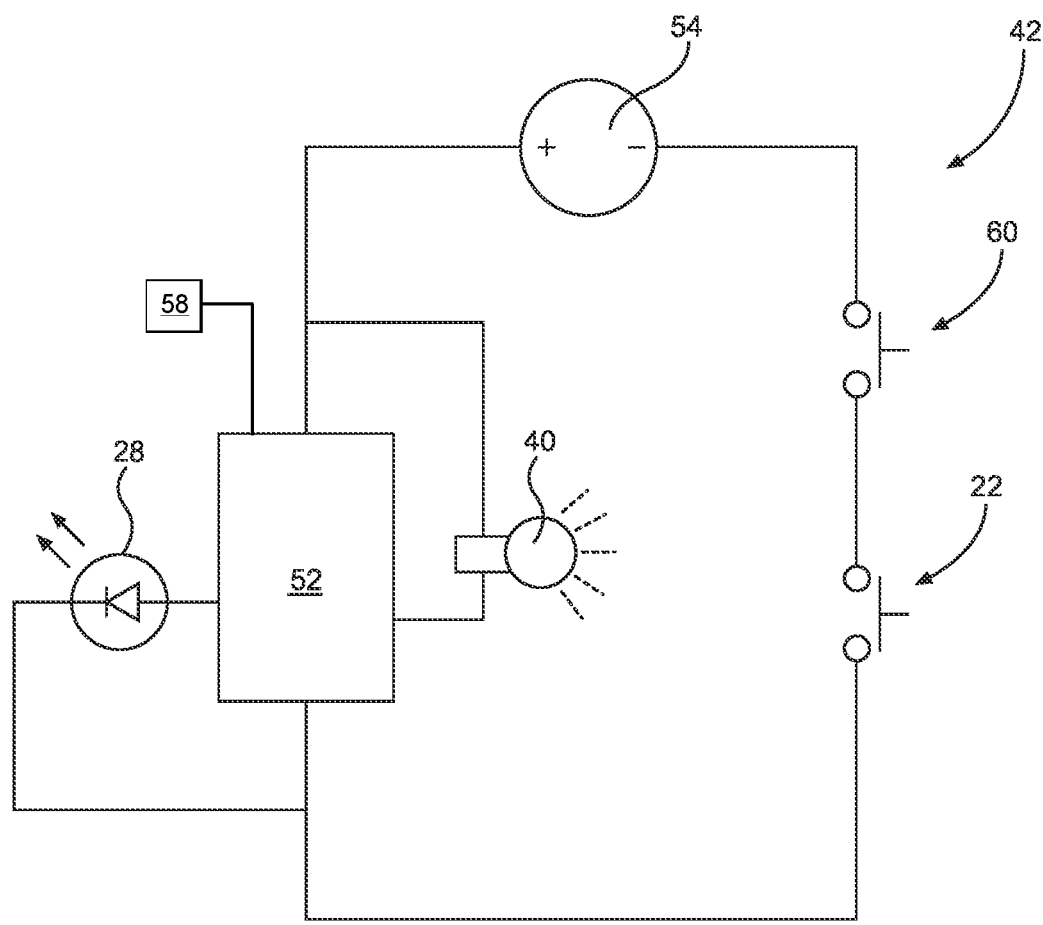
FIG. 7 is a schematic drawing of a control system for the hearing aid dryer and disinfection kit according to a preferred embodiment.
Figure 8:
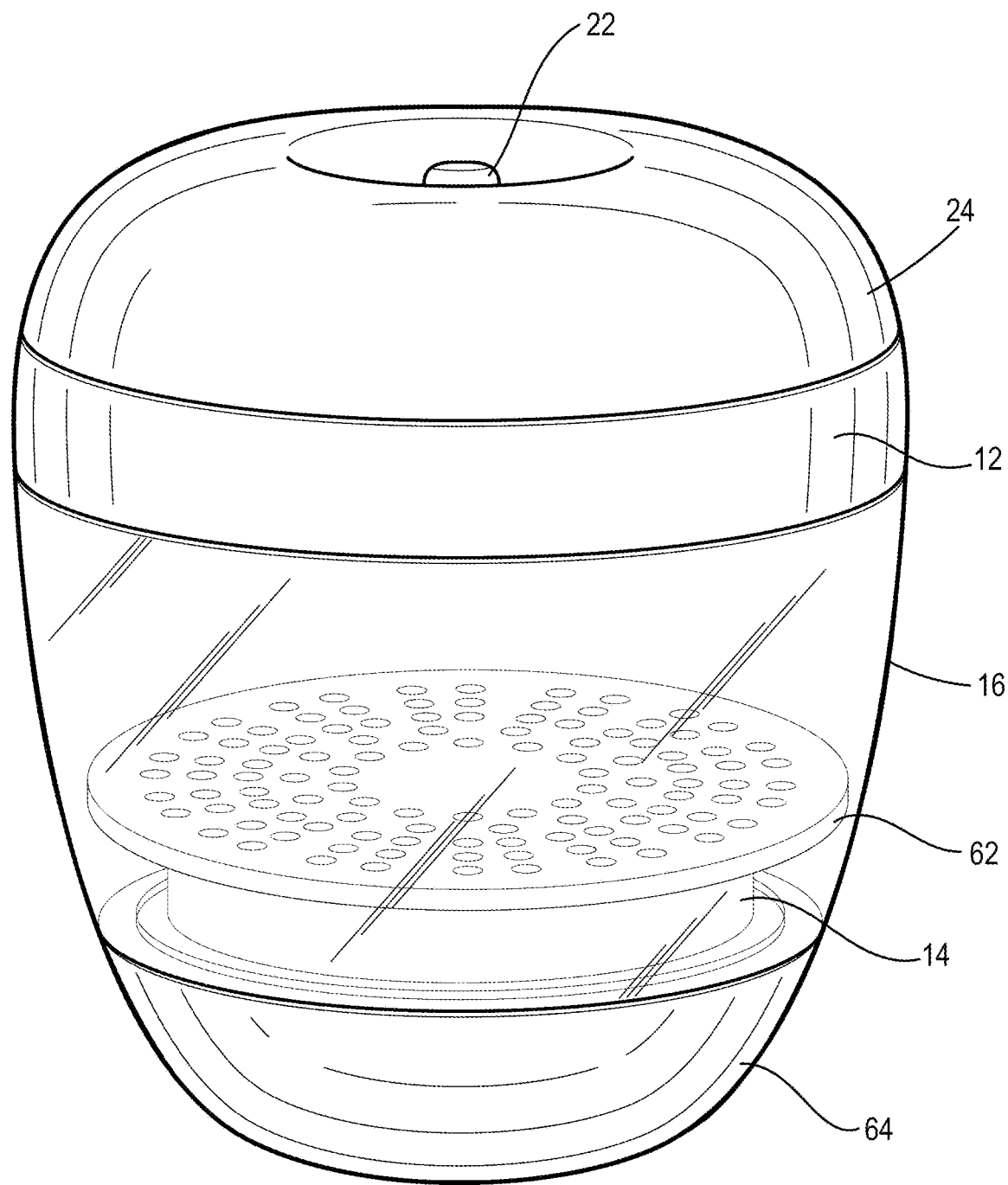
FIG. 8 is a perspective view of a hearing aid dryer and disinfection kit according to a second embodiment.

An important feature of the hearing aid dryer and disinfection device 10 is the lid 12. Non-limiting aspects of the lid 12 are illustrated in FIGS. 4-7 and include a disinfecting light source, such as an ultraviolet (UV) light source 40, and controller circuitry 52 therefor (FIG. 7). The UV light source 40 is disposed in an interior 44 of the lid 12 on a partition 46 that separates an interior portion 48 of the lid 12 from an electronic housing portion 50 of the lid 12. The UV light source 40 may provide direct irradiation of the hearing aids 18 to kill bacteria or the like on surfaces of the hearing aids 18. Also, ozone may be produced by the UV light source 40 to act as a deodorizer.

A suitable UV light source 40 is a UV-C lamp that is a high intensity 50 mm linear (253.7 nm) germicidal lamp rated at 70 uW/cm$^2$. The wavelength of 253.7 nanometers of the UV-C lamp is proven to inhibit colony formation in microorganisms which may significantly reduce itching and infection of the ear canal. In some embodiments, the disinfecting light source produces violet light in the 400-450 nm range to generate Reactive Oxygen Species (ROS) for killing bacteria.

In some embodiments, the UV light source 40 comprises one or more UV light emitting diodes (LEDs). In a preferred embodiment, multiple UV LEDs are distributed across the bottom surface of the lid 12 to evenly illuminate the interior 20 of the container 16.

The interior portion 48 of the lid 12 and the interior 20 of the container 16 may include a UV reflective coating or may be formed from a UV reflective material, such as e-PTFE (expanded polytetrafluoroethylene).

As set forth above, the indicator lamp 28 on the lid 12 is visible to the user and when illuminated indicates that the UV light source 40 is activated to warn the user not to open the lid 12 of the device 10 while the UV light source 40 is on. In a preferred embodiment, the indicator lamp 28 is a light-emitting diode (LED). The controller circuitry 52 may be activated by pressing the switch 22 which may be a capacitive switch or a micro-contact switch. If a capacitive switch is used, the lid 12 is devoid of any moving parts.

The controller circuitry 52 also includes a digital timer for controlling the illumination of the UV lamp 40 for a predetermined amount of time. The predetermined amount of time may range from a few minutes to several hours or longer.

A power source 54 (FIG. 7) such as a rechargeable or standard battery 56 may be included in the electronic housing portion 50 of the lid 12 to power the controller circuit 52, UV light source 40, and LED lamp 28. In some embodiments, a rechargeable battery is used as the power source 54 which may be charged by removing the battery 56 from the lid 12 or by means of a USB connection 58 disposed on the side portion 26 of the lid 12. In some embodiments, the power source 54 is provided through the USB connection 58 in the absence of an internal battery 56.

Many of the structural components of the device 10, including the lid 12, desiccant holder 14 and the container 16 may be made of a durable plastic material. In some embodiments, the container 16 may be made of glass or ceramic.

As shown in FIG. 7, some embodiments of the device 10 include lid removal detection circuitry 60 to detect that the lid 12 has been removed from the container, in which case the UV light source 40 is deactivated. The detection circuitry 60 may comprise a magnetic switch or metal contacts on the threads of the lid 12 and the container 16 that close the circuit powering the UV light source 40 when lid 12 is screwed down tightly.

It will be appreciated that the desiccant in the desiccant holder 14 loses its effectiveness after some number of drying cycles. In a preferred embodiment, the device 10 provides a reminder to the user when it is time to replace the desiccant holder 14 with a fresh one. To implement the reminder, the controller 52 counts the number of drying/disinfection cycles that have occurred since the most recent replacement of the desiccant holder 14. For example, if it is assumed that the device 10 will be used once a day for drying and disinfection, and if it is assumed that the desiccant holder 14 should be replaced at least every thirty days, then the device 10 should provide a change-out reminder after a particular desiccant holder 14 has been used in thirty drying/disinfection cycles.

In a preferred embodiment, the controller 52 increments a counter each time the cycle start switch 22 is pressed while the lid 12 is closed. When the counter reaches the change-out threshold count, such as thirty, the controller 52 generates an indication to the user that it is time to change out the desiccant holder 14. In one embodiment, the change-out indication comprises the indicator lamp 28 changing colors, such as from green to red. In an alternative embodiment, the change-out indication comprises a beeping tone or other audible indicator.

In some embodiments, the change-out reminder is provided in two stages. For example, the controller 52 may generate an initial change-out indication at 21 days into the drying/disinfection cycle, such as by changing the indicator lamp 28 from green to yellow, and then generate a final change-out indication at 30 days into the drying/disinfection cycle, such as by changing the indicator lamp 28 from yellow to red.

After the desiccant holder 14 has been replaced, and while the lid 12 is still open, the user may press and hold the cycle start switch 22, such as for five seconds, to cause the controller 52 to reset the cycle count to zero and change the indicator lamp 28 back to green.

In a preferred embodiment, the change-out threshold count is a programmable value that may be changed as needed depending on the characteristics of desiccant holder 14 in use. For example, if the manufacturer of the desiccant holder 14 increases the useful lifetime of the desiccant in the holder 14, the change-out threshold count may be reprogrammed to accommodate a greater number of cycles before the change-out reminder is generated. In some embodiments, the change-out threshold count may be reprogrammed in memory of the controller 52 via the USB connection 58, such as by using a software application running on a mobile computing device, such as a smart phone.

Second Embodiment

FIGS. 8, 9, 10A and 10B depict an electronic component dryer and disinfection device 10 according to a second embodiment. The device 10 includes a removable lid 12 having a removeable top portion 24, a container 16 for holding hearing aids or other electronic devices to be dried and disinfected, a UV-reflective tray 62 on which the hearing aids rest during a drying/disinfection cycle, a removable desiccant holder 14 containing desiccant, and a removeable bottom portion 64. The lid 12 may provide an air-tight seal when attached to the container 16 so that ambient moisture external to the device 10 is not introduced into the container 16. An O-ring type gasket may be included for this purpose.

The electrical components depicted in FIG. 7 and described previously, including the UV bulb 40, are preferably all disposed within or on the lid 12. Removable batteries 56 for powering the electrical components may be accessed by removing the top portion 24, which may be secured to the lid 12 by threads or other interlocking features. A drying/disinfection cycle is initiated by a cycle start switch 22 disposed on the top of the lid 12, the pushbutton portion of which extends through a central hole in the top portion 24.

Figure 9:
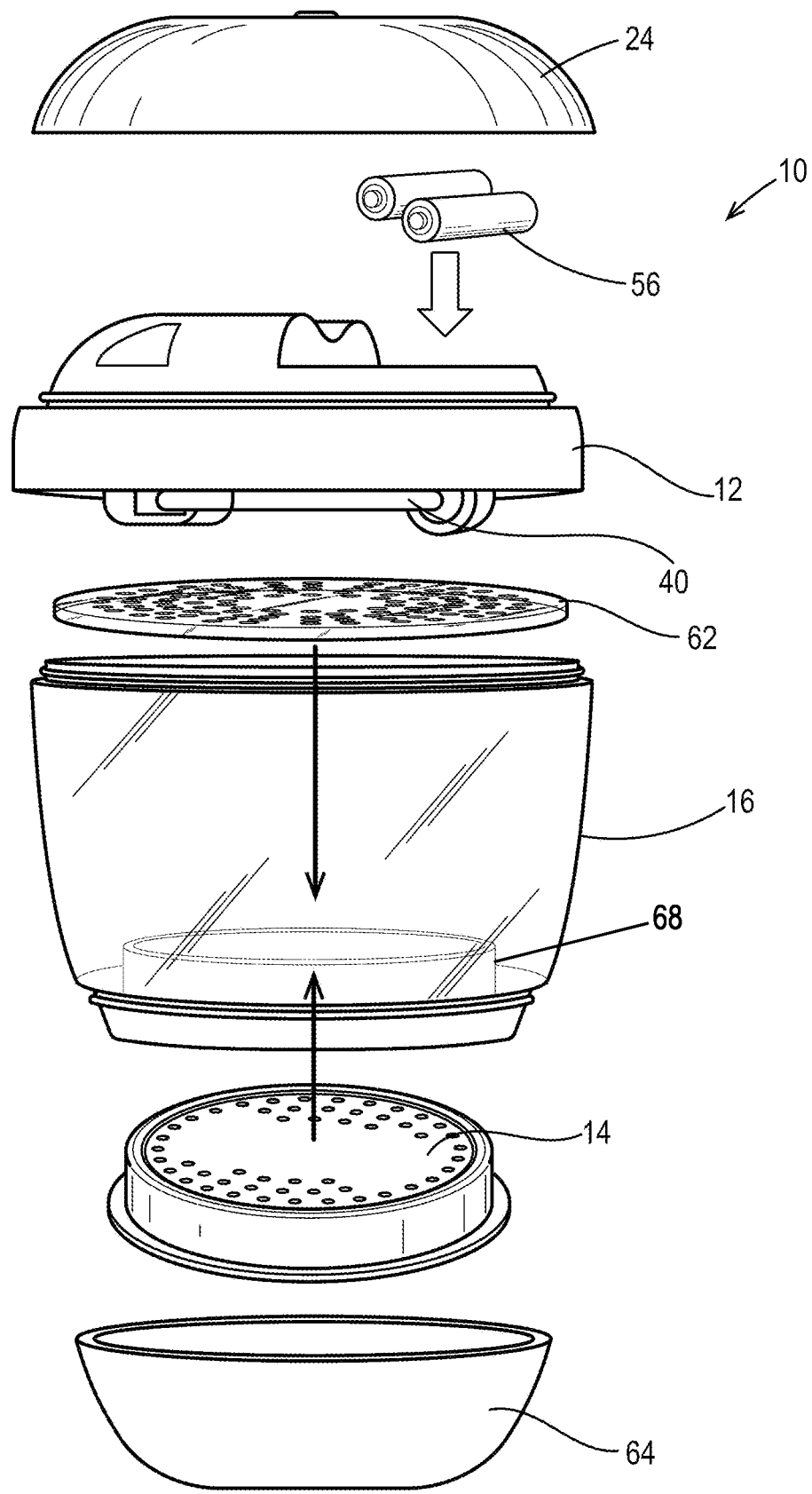
FIG. 9 is an exploded perspective view of the hearing aid dryer and disinfection kit of FIG. 8.

The container 16 is preferably molded from clear or smoky opaque polycarbonate so that the hearing aids may be observed during a drying cycle. As shown in FIG. 9, a cylindrical recess 68 is molded into the bottom of the container 16 for receiving the cylindrical desiccant holder 14. When fully inserted into the recess 68, the bottom flange of the desiccant holder 14 rests against the bottom lip of the container 16. The bottom portion 64 secures to the bottom lip of the container 16, such as using threads or other interlocking features, thereby retaining the desiccant holder 14 within the recess 68.

Figure 10A:
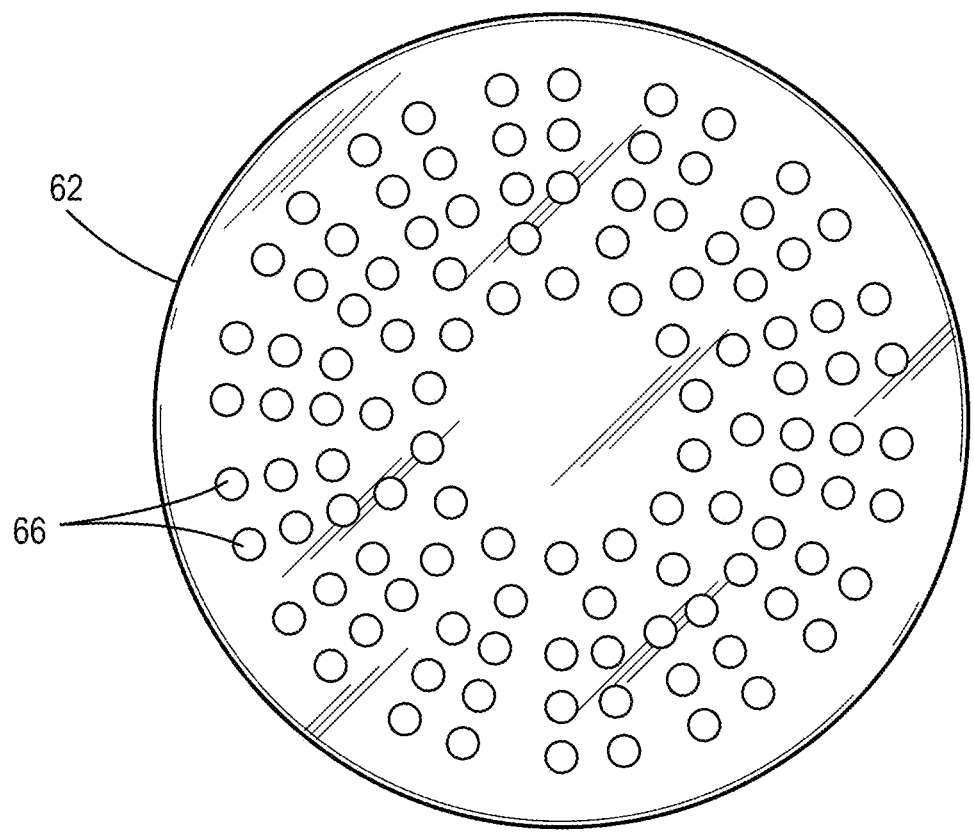
FIGS. 10A and 10B depict a tray of the hearing aid dryer and disinfection kit of FIGS. 8 and 9.
Figure 10B:
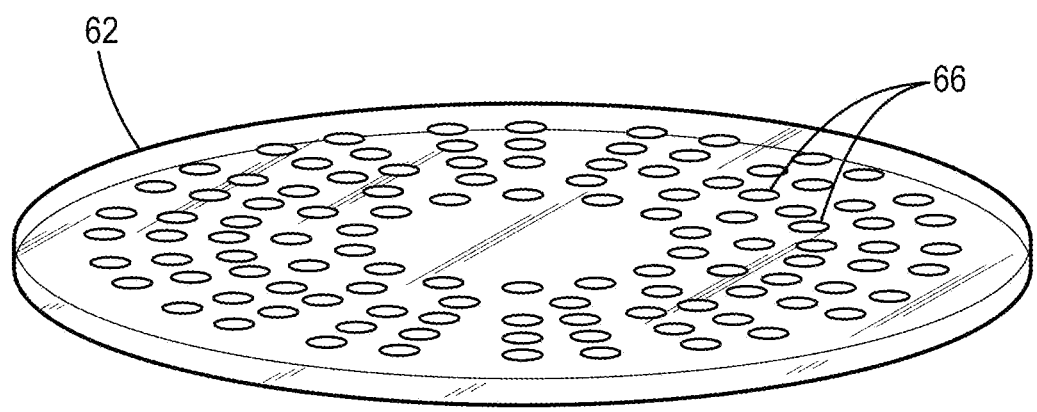

In a preferred embodiment, the tray 62 is a cylindrical disk molded from polycarbonate, and has a mirrored UV-reflective coating. The diameter of the tray 62 is preferably about three inches and is sized to fit snuggly within the interior of the container 16 when the tray 62 is resting upon the top lip of the recess 68. As shown in FIGS. 10A-10B, the tray 62 includes a pattern of holes 66 that provide air flow communication between the desiccant holder 14 and the hearing aids resting on top of the tray 62. The UV-reflective coating on the tray 62 increases the exposure of lower surfaces of the hearing aids to UV light as the light is reflected up from the upper surface of the tray. Without the reflective coating, those lower surfaces may otherwise be in shadow, and not receive sufficient exposure for disinfection.

In some embodiments, the tray 62 is removable and replaceable. In other embodiments, the tray 62 is fixedly secured within the interior of the container 16.

The invention has been described in detail with particular reference to preferred embodiments thereof, but it will be understood that variations and modifications will be affected with the spirit and scope of the invention.

What is claimed is:

1. A portable dryer and disinfection device comprising:
    a container having an interior for receiving one or more electronic components for drying and disinfection;
    a tray disposed within the interior of the container on which the one or more electronic components are placed for drying and disinfection, the tray including holes that provide air flow communication through the tray;
    a lid configured to be removably secured to an upper portion of the container;
    a cycle start switch disposed in the lid and isolated from the interior of the container, the cycle start switch including a pushbutton portion extending above an upper portion of the lid;
    an ultraviolet light source attached to a bottom portion of the lid, wherein ultraviolet light generated by the ultraviolet light source is directed into the interior of the container below the lid;
    one or more replaceable batteries disposed in a recess in an upper portion of the lid for providing electrical power to the ultraviolet light source;
    a controller circuit disposed within the lid and isolated from the interior of the container, the controller circuit configured to control the ultraviolet light source to operate during a drying and disinfection cycle;
    a top portion configured to be removably secured to the upper portion of the lid, the top portion including a central aperture through which the pushbutton portion of the cycle start switch extends when the top portion is secured to the upper portion of the lid, the top portion configured to be removed from the upper portion of the lid to provide access for removal and replacement of the one or more replaceable batteries;
    a removable desiccant holder disposed at least partially within the interior of the container below the tray; and
    a bottom portion configured to be removably secured to a bottom lip of the container, wherein the bottom portion is configured to be removed from the bottom lip of the container to provide access for removal and replacement of the removable desiccant holder.

2. The portable dryer and disinfection device of claim 1, wherein the controller circuit generates an indication that the desiccant holder is due for replacement.

3. The portable dryer and disinfection device of claim 2 further comprising an indicator lamp disposed on the lid, wherein the indication generated by the controller circuit comprises changing a property of light generated by the indicator lamp.

4. The portable dryer and disinfection device of claim 1, wherein the ultraviolet light source comprises one more ultraviolet light emitting diodes or one or more ultraviolet lamps.

5. The portable dryer and disinfection device of claim 1 further comprising lid removal detection circuitry that deactivates the ultraviolet light source upon removal of the lid from the container, wherein the lid removal detection circuitry comprises a magnetic switch or metal contacts on the container and on the lid that closes a circuit to provide power to the ultraviolet light source when lid is secured to the container.

6. The portable dryer and disinfection device of claim 1 wherein the tray is configured to be removable from the interior of the container.

7. The portable dryer and disinfection device of claim 1 wherein the tray has an ultraviolet-reflective coating on at least an upper surface thereof.

8. A portable dryer and disinfection device comprising:
    a container having an interior for receiving one or more electronic components for drying and disinfection;
    a tray disposed within the interior of the container on which the one or more electronic components are placed for drying and disinfection, the tray including holes that provide air flow communication through the tray;
    a lid configured to be removably secured to an upper portion of the container;
    an ultraviolet light source attached to a bottom portion of the lid, wherein ultraviolet light generated by the ultraviolet light source is directed into the interior of the container below the lid;
    one or more replaceable batteries disposed in a recess in an upper portion of the lid for providing electrical power to the ultraviolet light source;
    a top portion that is removably secured to the upper portion of the lid, the top portion configured to be removed from the upper portion of the lid to provide access for removal and replacement of the one or more replaceable batteries;
    a removable desiccant holder disposed at least partially within the interior of the container below the tray; and
    a bottom portion configured to be removably secured to a bottom lip of the container, wherein the bottom portion is configured to be removed from the bottom lip of the container to provide access for removal and replacement of the removable desiccant holder.

9. The portable dryer and disinfection device of claim 8, further comprising:
 a cycle start switch disposed in the lid and isolated from the interior of the container, the cycle start switch including a pushbutton portion extending above the upper portion of the lid; and
 the top portion including a central aperture through which the pushbutton portion of the cycle start switch extends when the top portion is secured to the upper portion of the lid.

10. The portable dryer and disinfection device of claim 8 further comprising a controller circuit disposed within the lid and isolated from the interior of the container, the controller circuit configured to control the ultraviolet light source to operate during a drying and disinfection cycle.

11. The portable dryer and disinfection device of claim 10, wherein the controller circuit generates an indication that the desiccant holder is due for replacement.

12. The portable dryer and disinfection device of claim 11 further comprising an indicator lamp disposed on the lid, wherein the indication generated by the controller circuit comprises changing a property of light generated by the indicator lamp.

13. The portable dryer and disinfection device of claim 8 further comprising lid removal detection circuitry that deactivates the ultraviolet light source upon removal of the lid from the container, wherein the lid removal detection circuitry comprises a magnetic switch or metal contacts on the container and on the lid that closes a circuit to provide power to the ultraviolet light source when lid is secured to the container.

14. The portable dryer and disinfection device of claim 8 wherein the tray is configured to be removable from the interior of the container.

15. The portable dryer and disinfection device of claim 8 wherein the tray has an ultraviolet-reflective coating on at least an upper surface thereof.

16. A portable dryer and disinfection device comprising:
 a container having an interior for receiving one or more electronic components for drying and disinfection;
 a tray disposed within the interior of the container on which the one or more electronic components are placed for drying and disinfection, the tray including holes that provide air flow communication through the tray;
 a lid configured to be removably secured to an upper portion of the container;
 a cycle start switch disposed in the lid and isolated from the interior of the container, the cycle start switch including a pushbutton portion extending above an upper portion of the lid;
 an ultraviolet light source attached to a bottom portion of the lid, wherein ultraviolet light generated by the ultraviolet light source is directed into the interior of the container below the lid;
 one or more replaceable batteries disposed in an upper portion of the lid for providing electrical power to the ultraviolet light source;
 a controller circuit disposed within the lid and isolated from the interior of the container, the controller circuit configured to control the ultraviolet light source to operate during a drying and disinfection cycle;
 a top portion including a central aperture through which the pushbutton portion of the cycle start switch extends when the top portion is secured to the upper portion of the lid;
 a removable desiccant holder disposed at least partially within the interior of the container below the tray; and
 a bottom portion configured to be removably secured to a bottom lip of the container, wherein the bottom portion is configured to be removed from the bottom lip of the container to provide access for removal and replacement of the removable desiccant holder.

17. The portable dryer and disinfection device of claim 16, wherein
 the one or more replaceable batteries are disposed in a recess in the upper portion of the lid, and
 the top portion is configured to be removed from the upper portion of the lid to provide access for removal and replacement of the one or more replaceable batteries.

18. The portable dryer and disinfection device of claim 16 further comprising lid removal detection circuitry that deactivates the ultraviolet light source upon removal of the lid from the container, wherein the lid removal detection circuitry comprises a magnetic switch or metal contacts on the container and on the lid that closes a circuit to provide power to the ultraviolet light source when lid is secured to the container.

19. The portable dryer and disinfection device of claim 16 wherein the tray is configured to be removable from the interior of the container.

20. The portable dryer and disinfection device of claim 16 wherein the tray has an ultraviolet-reflective coating on at least an upper surface thereof.

* * * * *